United States Patent [19]

Bailin et al.

[11] Patent Number: 5,207,226
[45] Date of Patent: May 4, 1993

[54] DEVICE AND METHOD FOR MEASUREMENT OF BLOOD FLOW

[75] Inventors: Steven J. Bailin, West St. Paul; Robert F. Wilson, Shoreview, both of Minn.

[73] Assignee: Regents of the University of Minnesota, St. Paul, Minn.

[21] Appl. No.: 646,110

[22] Filed: Jan. 25, 1991

[51] Int. Cl.$^5$ ............................................. A61B 5/027
[52] U.S. Cl. ........................... 128/661.08; 128/662.06; 128/692; 604/96; 604/104
[58] Field of Search .................. 128/691, 692, 661.08, 128/662.06, 662.04; 604/96, 104

[56] References Cited

U.S. PATENT DOCUMENTS

| | | | |
|---|---|---|---|
| 3,605,726 | 9/1971 | Williams et al. | 128/691 |
| 3,902,501 | 9/1975 | Citron et al. | 128/785 |
| 4,169,464 | 10/1979 | Obrez | 604/281 X |
| 4,269,198 | 5/1981 | Stokes | 128/785 |
| 4,355,643 | 10/1982 | Laughlin et al. | 128/663 |
| 4,502,488 | 3/1985 | Degironimo et al. | 128/692 |
| 4,665,911 | 5/1987 | Williams et al. | 128/204.21 |
| 4,667,678 | 5/1987 | Croshie et al. | 128/661.08 |
| 4,671,295 | 6/1987 | Abrams et al. | 128/663 |
| 4,722,347 | 2/1988 | Abrams et al. | 128/663 |
| 4,730,619 | 3/1988 | Koning et al. | 128/419 PG |
| 4,733,669 | 3/1988 | Segal | 128/662.04 |
| 4,791,935 | 12/1988 | Baudino et al. | 128/692 X |
| 4,793,825 | 12/1988 | Benjamin et al. | 604/891.1 |
| 4,873,989 | 10/1989 | Einzig | 128/692 |
| 4,878,898 | 11/1989 | Griffin et al. | 604/101 |
| 4,886,059 | 12/1989 | Weber | 128/207.15 |
| 4,887,996 | 12/1989 | Bergmark | 604/281 X |
| 4,913,642 | 4/1990 | Weber | 425/275 |
| 4,957,110 | 9/1990 | Vogel et al. | 128/692 X |
| 5,121,749 | 6/1992 | Nassi et al. | 128/692 |

OTHER PUBLICATIONS

Melvin L. Marcus, The Coronary Circulation in Health and Disease, pp. 28-34.
Robert F. Wilson, et al, Transluminal, Subselective Measurment of Coronary Artery Blood Flow Velocity and Vasodilator Reserve in Man, Jul. 1985.
D. Laughlin, et al., New Construction Methods for a Family of Doppler Transducers, 1985.
R. F. Wilson, et al., Doppler Echocardiography in Aortic, Coronary and Myocardial Disease as well as Congenital Lesions, 1987.
Craig J. Hartley and Huntley D. Millar, Ultrasonic Sensors for Measuring Coronary Blood Flow, Jan. 1988.

*Primary Examiner*—Randall L. Green
*Assistant Examiner*—Mary Beth O. Jones
*Attorney, Agent, or Firm*—Robert A. Elwell; Harold D. Jastram

[57] ABSTRACT

A device and method for measuring fluid flow within a vessel having fluctuating elastic walls, such as, for example, an artery. The device includes a catheter; an internal stablizer or frame for establishing an invariant cross-section in the vessel wall; and a fluid velocity detecting system, such as, for example, a Doppler crystal transducer. The method for measuring includes the steps of stabilizing the vessel wall and measuring the velocity of fluid passing through the stabilized cross-section of the vessel wall. A method of treating and a method of diagnosing vascular disease by employing the device of this invention is also part of the invention.

23 Claims, 7 Drawing Sheets

DEVICE AND METHOD FOR MEASUREMENT OF BLOOD FLOW

BACKGROUND OF THE INVENTION

The present invention relates to a device and method for measuring fluid flow and, in particular, relates to a device and method for measuring instantaneous fluid flow within a vessel characterized by a fluctuating elastic wall. One example of such a vessel is an arterial vessel.

A significant challenge to modern medicine concerns accurate measurement of instantaneous blood flow through an arterial vessel. Accurate measurements of such blood flow would contribute to enhanced assessment of vascular status and improved diagnosis of a variety of vascular diseases. Improved diagnosis and enhanced assessment of vascular status should facilitate more effective disease treatments.

Another major challenge is the measurement of instantaneous flow into various distinct regions or portion of pulmonary vasculature.

Several methods for measuring blood flow are already available to the art. One method involves measurement of blood flow by placing an electromagnetic flow meter around a blood vessel or on a graft. Such a method has been generally limited to blood flow measurements during surgery. The method also undesirably requires surgical access to the exterior of the blood vessel or installing a graft.

Another method for measuring blood flow involves attaching a Doppler crystal to the end of the catheter and maneuvering the end of the catheter into the artery. The various Doppler crystal systems provide accurate blood velocity information. But as a method for flow measurement, Doppler systems are limited by measuring velocity but not cross-sectional area. Consequently, measurements of velocity may not reflect true volumetric flow if the arterial wall is elastic. Most arteries, however, are characterized by elastic walls and because cardiac output is pulsed into the elastic walls and arteries are muscular tubes that have a variable amount of tone. Hence, the cross-section of the artery fluctuates. Since flow is a function of both fluid velocity and cross-sectional area, improved velocity measurements fail to improve the measurement of flow.

Because the pulmonary arteries are thin and very elastic, a particularly challenging problem in blood flow measurement concerns the measurement of flow to various portions or segments of the vasculature serving the lungs. There have been suggestions that dysfunctions in the vasculature; for example, hypertension, sclerosing, or occluding of arteries, tends to occur heterogeneously rather than homogeneously within the lungs. Further, it has been suggested that blood flow has a tendency to favor lower regions or portions of the lungs relative to upper portions of the lungs, in a gravity dependent fashion. To date, however, most pulmonary blood flow assessments have been performed on the entire pulmonary blood flow rather than a localized region of the lung.

Catheters capable of maintaining a constant position within an artery are known, however, such catheters do not stabilize the cross-sectional area within the artery.

SUMMARY OF THE INVENTION

Although Doppler techniques for the measurement of cardiac output exist, the development of a Doppler catheter able to selectively measure instantaneous blood flow in individual pulmonary artery segments would aid in the evaluation of disease affecting the pulmonary vasculature by permitting selective measurement of segmental pulmonary vasculature resistance. Direct measurement of blood flow velocity in segmental pulmonary arteries, however, is complicated by highly elastic walls, variable vessel, geometry, and further affected by respiratory motion and cardiac motion artifacts.

The present invention includes a device, suitable for measuring fluid flow within a vessel characterized by segments of elastic wall, each of the wall segments fluctuating and defining a variable cross-section for the segment. The device includes a catheter having a distal end suitable for insertion into the vessel. A means for internally stabilizing a segment of vessel wall is carried by the catheter adjacent the distal end. A means for detecting fluid velocity within the stabilized segment of wall is also carried by the catheter adjacent the distal end. In a preferred embodiment of the present invention, the device involves a loop or frame mounted adjacent the distal end of the catheter and a piezoelectric crystal transducer adjacent the loop or frame. The frame is oriented such that its perimeter engages the segment of wall to be stabilized. The frame has sufficient rigidity to secure a constant geometry and dimension without substantially obstructing fluid flow through the segment. In other words, the reinforcing frame serves to stabilize the wall segment by rigidly supporting the interior surface of the wall, thereby providing a stable cross-section within which to measure fluid velocity. Providing a constant cross-section and accurately measuring fluid velocity passing through the cross-section allows for the accurate measurement of flow and particularly instantaneous blood flow. Preferably and optionally, the device includes a pressure measurement system, such as for example a micromanometer. The availability of pressure data to accompany the cross-sectional area and accurate velocity information allows for accurate measurement of resistance within the portion of pulmonary vasculature downstream from the stabilized segment. Optionally and preferably, the device further includes a longitudinal channel within the catheter. The longitudinal channel extends from an outlet adjacent to the distal end and a fitting or connector adjacent the proximal end of the catheter. Such a channel allows for the controlled delivery of a pharmaceutical or biological agent such as a vasoconstrictor or a vasodilator. Another or the same longitudinal fluid-filled channel allows for measurement of pressure at the distal end of the catheter by attachment of a pressure tranducer to the proximal end.

In another embodiment of the present device, the means for internally stabilizing a segment of vessel wall is a helical structure, which serves to stabilize and support a segment of wall and provide an invariant cross-section in which a velocity measurement may be performed, thereby providing accurate instantaneous flow measurements past the stabilized segment.

In yet another embodiment, the means for stabilizing a segment of wall are further provided with a means for retracting so as to facilitate placement of the distal end of the catheter at a selected segment of vessel. Devices with a retractable stabilizer feature may facilitate device placement and removal.

Additionally, the present invention includes a method for measuring blood flow in an arterial vessel serving a selected section of pulmonary vasculature. The method includes the steps of stabilizing a segment of wall in the arterial vessel serving the section of pulmonary vasculature and measuring the velocity of blood flow passing within the stabilized portion. Preferably, the method further includes inserting a wall stabilizer, such as, for example, by employing the earlier mentioned devices of this invention, into the vessel and advancing the wall stabilizer to a segment of wall to be stabilized. By also measuring pressure, the resistance to blood flow may also be measured.

The present invention also includes a method of treating localized pulmonary hypertension in a section of pulmonary vasculature by stabilizing a segment of vessel wall in the arterial vessel serving the section of pulmonary vasculature, measuring the blood velocity through the stabilized section and selectively infusing a pharmaceutical or biological agent into the blood flow to the section of pulmonary vasculature. Preferably, the method of treating localized pulmonary hypertension further includes the step of calculating resistance to blood flow in the segment of pulmonary artery based upon the pulmonary artery pressure in the segment and the calculated blood flow. Preferably, the method of treating hypertension further includes remeasuring the blood velocity through the stabilized portions subsequent to infusing the pharmaceutical agent.

BRIEF DESCRIPTION OF THE DRAWINGS

FIG. 4a is a schematic view of another embodiment of the invention.

FIG. 4b is an schematic axial view of the distal portion of the device of FIG. 4a.

FIG. 7b is an axial view of the device of FIG. 7a.

DETAILED DESCRIPTION OF THE INVENTION

Figure 1:
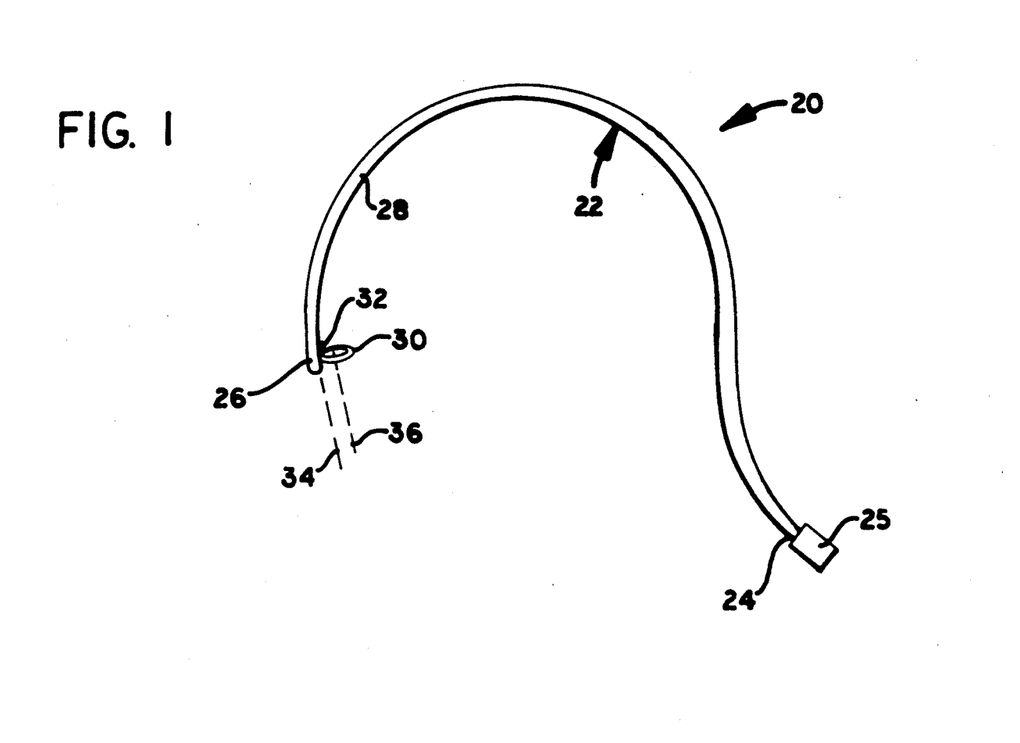
FIG. 1 is a schematic plan view of a device of the present invention.

A device of this invention is generally shown at 20 in FIG. 1. The device includes a catheter 22 having a proximal end 24 and a distal end 26. A catheter body 28 extends between the proximal end 24 and the distal end 26. A suitable length of body 28 is roughly 135 cm. Suitable materials for the body 28 include polyethylene, polyurethane, or woven dacron. Preferably, the body 28 includes 2 or more lumen 41 and has an exterior diameter of from about 3 F (French size) to about 8 F (1.0 mm to 2.7 mm), most preferably about 4 F (1.3 mm). Most preferably, the preferred 4 F body 28 also gradually tapers to about 3 F (1.0 mm) over about a 15 cm region including the distal end 26. The body 28 is flexible, yet when placed within a confined vessel may be advanced through the vessel. Catheters, particularly steerable catheters, are generally known in the art. In a preferred embodiment, the catheter 22 includes a guide wire for facilitating selective direction of the distal end 26 through the various vessels of a subject.

Additionally, the device 20 includes a frame 30 carried by the catheter 22 adjacent the distal end 26. Additionally, the device 20 includes a piezoelectric crystal transducer 32 carried on the catheter 22 adjacent the distal end 26. Preferably, the transducer 32 is located on the body 28 about 1-8 mm from the distal end 26. A variety of piezoelectric crystals may be employed in the transducer 32. Suitable operating frequencies for the transducer 32 range from about 1-30 MHz. Preferably, the transducer 32 includes a 10 MHz ceramic Doppler crystal. A 20 Mhz Doppler also is suitable. A connector 25 is schematically depicted at the proximal end 24. Again, a variety of connectors for catheters are generally known in the art. Suitable connectors and Doppler meters for connection to the device 20 are available from Millar Instruments, Inc. of Houston, Tex. Suitable catheters which may be used to prepare the device 20 are available from United States Catheter and Instrument, Co. (USCI).

A suitable transducer 32 may be installed on a catheter 22 as follows: A pair of insulated copper wires (for example about 38 gauge) are passed longitudinally through one of the lumen of the body 28 of the catheter 22 and then lead outward through a small opening, preferably a V-notch opening, in the body 28 of the catheter 22. Preferably, the opening is about 1 mm from the distal end 26. To increase flexibility of the wires, it is advantageous to solder short (e.g. 1 cm) thin (e.g. 48 gauge) gold leads to the ends of the wires protruding from the V-notch opening. These gold leads preferably are conductively attached to opposite sides of a fine-ground compressional piezoelectric crystal through the use of a conductive epoxy, (e.g. epoxy containing fine metallic silver powder in an amount sufficient to provide a conductive bond between the gold lead and the crystal).

Preferably, the piezoelectric crystal is about 0.7 mm to about 1.0 mm by about 0.7 mm to about 1.0 mm and has one side gold plated. A suitable 10 or 20 MHz crystal may be obtained from Valpey-Fischer, Inc. The back of the crystal should be coated with a 180 degree lens of epoxy (e.g. No. 795-Hy-Sol). The wires should be pulled at their proximal end to draw the attached leads and piezoelectric crystal of the transducer 32 to or partially into the V notch. The crystal is oriented on the catheter 22, preferably at an angle of from 30 to 45 degrees to the longitudinal axis 34, such that the transducer 32 when operated sends and receives ultrasonic frequencies to and from a space adjacent the distal end 26, and specifically, the transducer 32 orientation should generally allow ultrasonic sampling of the velocity of any blood flowing through the frame 30.

The crystal and V-notch opening preferably should be sealed with epoxy (e.g. No. 795-Hy-Sol) to secure the transducer and to fill any voids remaining at the V-notch opening. Epoxy, used in attaching the transducer may be hardened by heating the entire catheter to about 70 C for about 30 minutes. Preferably, any rough edges should be smoothed, for example by filing, to return the catheter 22 to a profile similar to its original profile.

The R. F. Wilson, et al. article *TRANSLUMINAL, SUBSELECTIVE MEASUREMENT OF CORONARY ARTERY BLOOD FLOW VELOCITY AND VASODILATOR RESERVE IN MAN;* Circulation vol 72 page 82 1985, incorporated herein by reference, may be consulted for earlier examples as well as background in the preparation and use of Doppler catheters. The Wilson article also explains appropriate Doppler meters to which the opposite ends of the copper wires should be connected. Doppler meters and Doppler catheters are also available from Millar Instruments, Inc. of Houston, Tex. and from NuMed, Inc. of Hopkinton, N.Y. The catheters from NuMed and Millar require at least the addition of frames as described herein to function as devices of this invention. It includes a 20 MHz crystal about 5 mm from its distal tip or end and has a 120 cm 4.5 F (1.5 mm) double lumen polyurethane body with a taper to 3 F (1.0 mm) in the final 15 cm approaching the distal tip.

The frame 30 is oriented to provide an aperture or open cross-section perpendicular to the longitudinal axis 34 of the catheter 22 in the region of the distal end 26. In a particularly preferred embodiment the frame 30 is annular and had an axis 36 parallel to the longitudinal catheter axis 34 of the body 28 adjacent the distal end 26.

The frame 30 is attached to the catheter body 28 by epoxy adhesive at the periphery 38. A strong structural relationship between the frame 30 and the catheter body 28 may be achieved by forming the frame 30 as a loop at the end of a short (e.g. 5 cm) length of wire (e.g. 20 gauge wire) and inserting the tail or remaining wire into the catheter body 28 at or near (e.g. within about 5 mm) the distal end 26. The tail of the wire loop, which will serve as the frame 30, may be bent or deformed, after insertion in the catheter, to achieve a perpendicular orientation of the resulting frame 30 relative to the catheter body 28. Further, the frame 30 should provide an aperature coinciding with the sampling area of the transducer 32.

Figure 2:
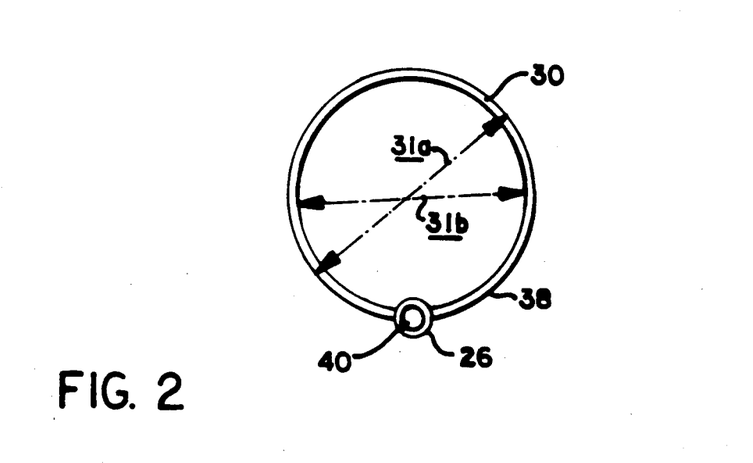
FIG. 2 is an enlarged schematic axial view of the distal portion of the device of FIG. 1.

The outside diameter 31a, as shown in FIG. 2, of the frame 30 should equal or slightly exceed the maximum expansion occuring in the artery segment to be measured when a pulse of blood from the heart passes ("systolic diameter"). The inner diameter 31b of the frame 30 should not significantly obstruct or prevent blood flow. Preferably, the cross-sectional area of the catheter body 28 adjacent the frame 30 together with the cross-section of the frame 30 (i.e. the difference in area subsumed between the outside diameter 31a and the inside diameter 31b) do not exceed about 25% of the systolic diameter. Typically, for measuring flow in pulmonary artery segments, the outside diameter 31a of the frame 30 ranges from about 0.5 mm to about 1.5 mm and, as earlier explained, depends upon the size of the artery in which measurements of velocity, flow and, optionally, pressure are to be performed.

Alternative embodiments of the annular frame 30 may be formed by generating a loop directly in the body 28 of a finely tapered or narrow catheter 22 at the distal end 26. Such a frame 30 can be generated by heat forming a suitable loop in the plastic of the catheter 22. Alternatively, a wire may be fully inserted longitudinally into the distal end 26 of the catheter 22 and then bent to form a frame 30. In yet another embodiment, a resilient loop structure may be formed in the end of a long wire. The loop may be temporily straightened as it is inserted at the connector 25 into a lumen or channel of a catheter lacking a fixed loop. The wire is advanced through the lumen and upon exiting at an orifice at the distal end 26, resumes its loop structure, thereby providing a frame 30 carried by the catheter capable of stabilizing vessel wall to allow accurate instantaneous measurement of blood flow.

Preferably, pressure sensor 40 is also present at the distal end 26 of the catheter 22. Catheters 22 carrying suitable pressure sensors and Doppler crystal transducers are also available from -Millar Instruments, Inc. of Houston, Tex. on a custom basis in sizes from 4 F (1.33 mm) to 7 F (2.33 mm). Alternatively, a fluid filled lumen of the catheter 22 can be monitored at the connector 25 at the proximal end measure pressure by a micromanometer 37.

Figure 3:
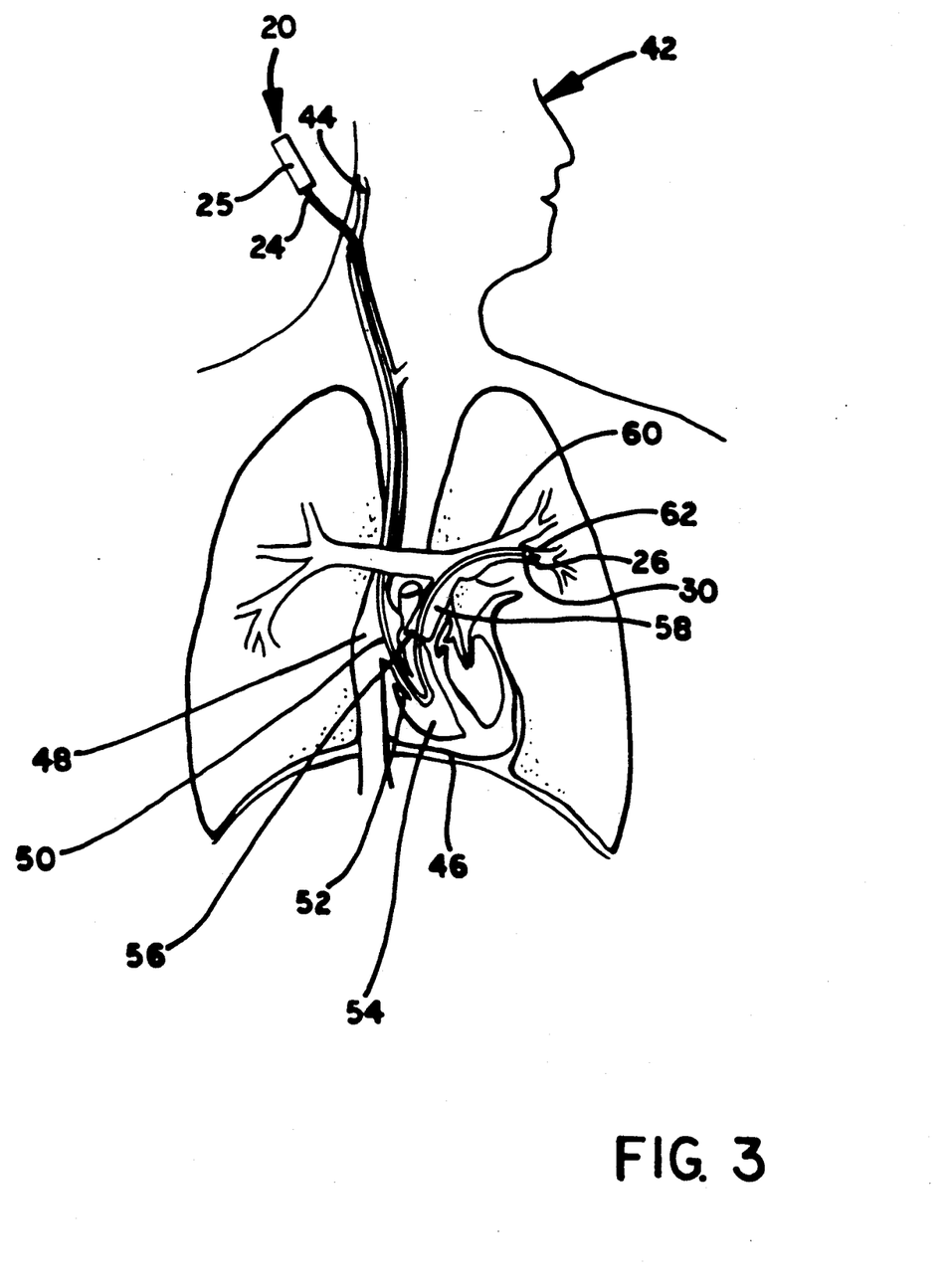
FIG. 3 is a schematic view of the device shown positioned to measure blood flow to a portion of pulmonary vasculature in a subject.

The device 20 may be installed in a subject 42, as schematically shown in FIG. 3, as follows. First, the distal end 26 of the device 20 is inserted into a major vein 44 of the subject 42 at an easily accessible location, such as, for example, in the neck region of the subject 42. Next, the distal end 26 is advanced through the vein 44 toward the heart 46. The distal end 26 is then advanced through the superior vena cava into the right atrium 50, through the tricuspid valve 52 into the right ventricle 54, through the pulmonary valve 56 and into the pulmonary trunk 58. By means of a guide wire, the distal end 26 may be steered and advanced into a desired artery, such as, for example, the left pulmonary artery 60 and into a branch artery 62 of the pulmonary artery.

An appropriately sized frame 30 at the distal end 26 engages the wall of a segment of the branch artery 62. The frame 30 stabilizes and supports the interior of the segment of wall in the branch 62 so as to provide an invariant cross-sectional area. Velocity measurements provided by the piezoelectric crystal Doppler transducer adjacent to the frame 30 then allows for an accurate measurement of the blood flow into the portions or regions of the lung served by the branch artery 62.

Figures 4A, 4B:
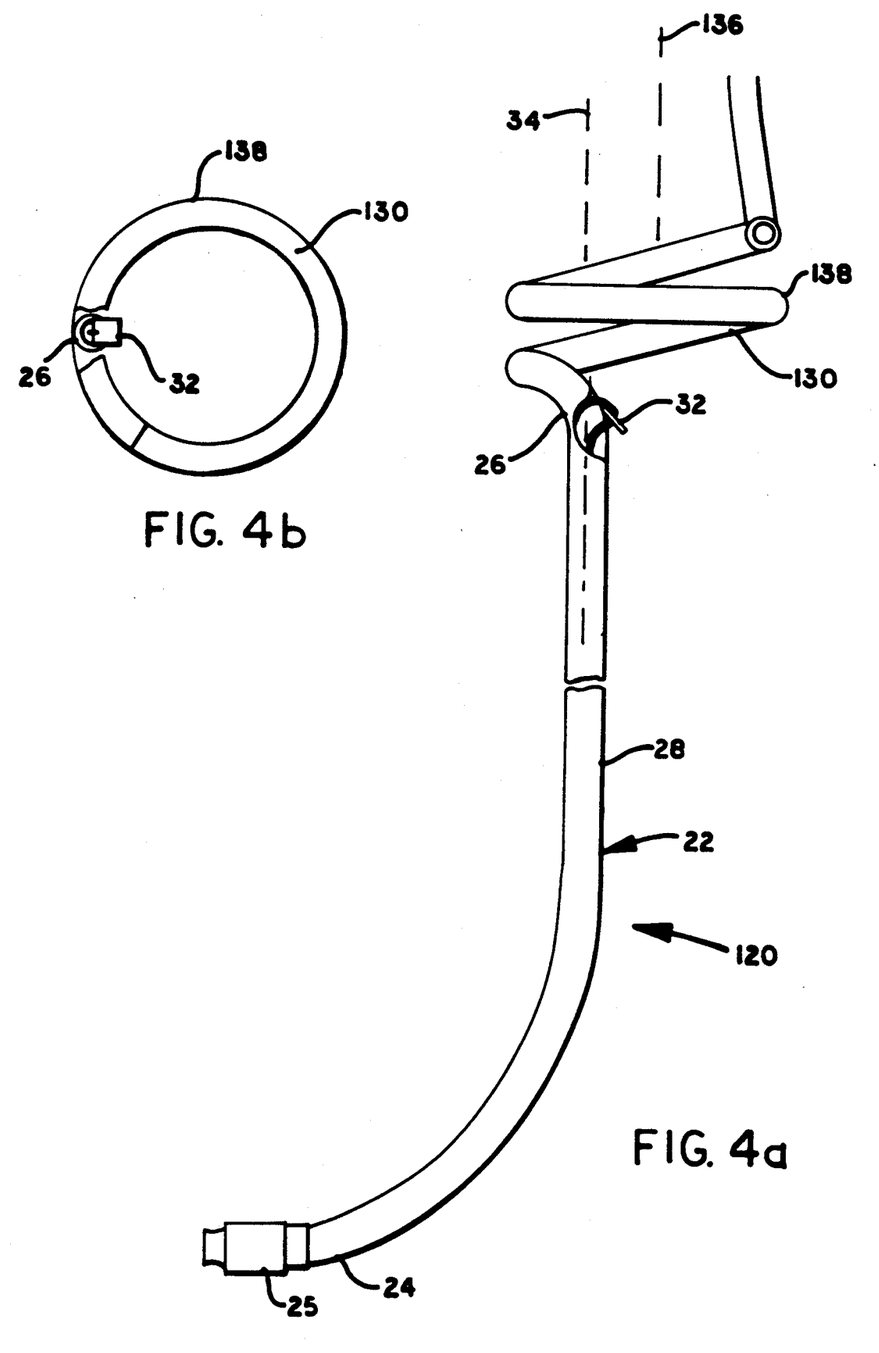

In another embodiment 120 as show in FIG. 4, a helical structure 130 is substituted for the earlier described frame 30. The helical structure 130 has a helical axis 136 lying parallel to the axis of the catheter body 28 near the distal end 26. The helical structure 130 has a helical radius 131 (i.e. the distance between the helical axis 136 and the periphery 138 of the helical structure 130). The helical structure also serves to internally support a segment of vessel wall and provide an invariant cross-sectional area within which flow velocity measurements may be made. Because the helical structure 130 provides a stable or invariant cross-sectional area, accurate blood flow measurements may be measured.

Figure 5:
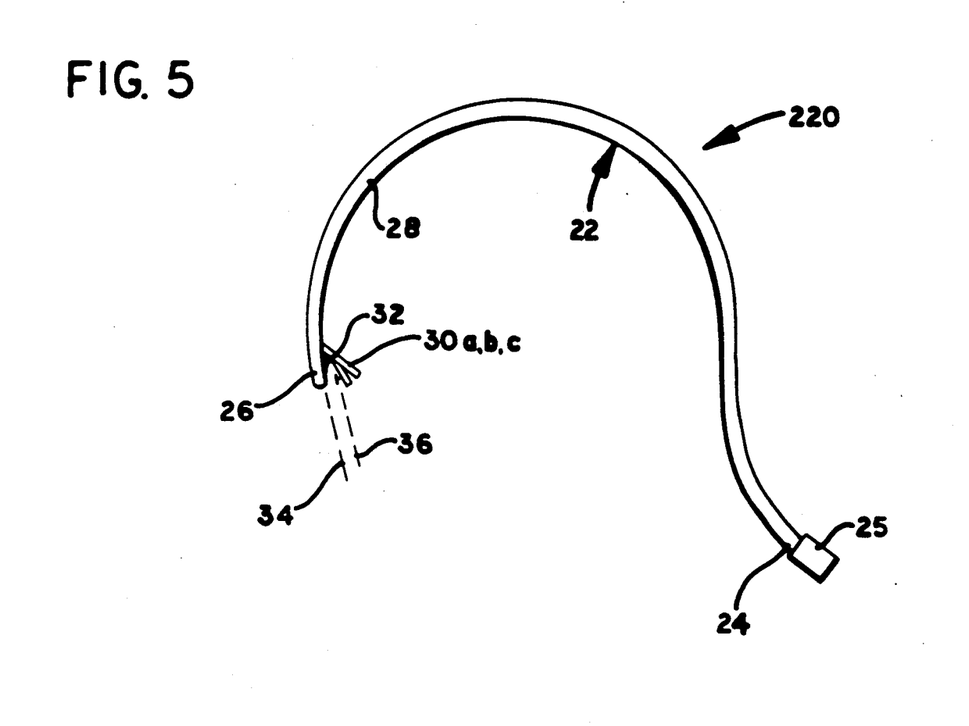
FIG. 5 is a schematic plan view of another embodiment of the invention.
Figure 6:
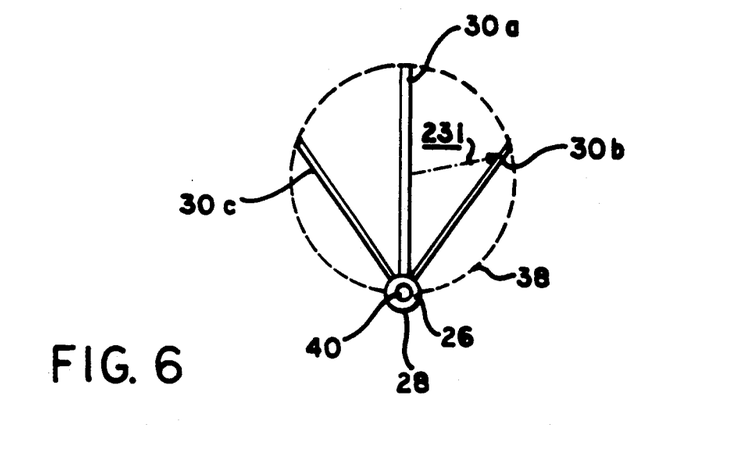
FIG. 6 is a schematic axial view of distal portion the device of FIG. 5.

In another embodiment schematically shown in FIG. 5, radially expanding wall engagement members 30a, 30b and 30c, are attached to the catheter body 28 adjacent the distal end 26. The engagement members 30a, 30b, and 30c support the interior of the vessel wall at a number of points to stabilize the cross-sectional area within the wall. Note that the catheter body 28 adjacent the distal end 26 also serves to support and stabilize a portion of the vessel wall. An axial view of this embodiment is shown in FIG. 6.

In a further refinement of the present invention, the frame 30, helix 131, or support members 30a, 30b, and 30c may be initially retracted to reduce the profile of the catheter 22 adjacent the distal end 26. One particularly preferred embodiment involving a retraction feature (schematically depicted as 33) is described with reference to the helical structure 131 as follows. The helical structure 131 is formed of a super-elastic material which may be transformed by temperature changes between two different crystal structures. The best known example of such a material is the Nickel-Titanium alloy which undergoes a transformation in crystal structure between the relatively strong, high temperature form known as Austenite to the weaker, low temperature crystal form Martensite. Such material is available in a biocompatible form from Shape Memory Applications, Inc. of Sunnyvale, Calif. which is a distributor of Nickel-Titanium alloys manufactured by Furukawa Electric Company, Ltd. The temperature change required to generate the change from a retracted form of helix to a expanded or supporting form of helix may be provided by electrically conductive wires leading from each end of the helical structure, into the catheter 22 and out at the connector 25. At a time during the installation of the distal end 26 and the retracted helix 130, provision of a temperature generating electrical current to the helix 130 expands the helical radius from the retracted condition to a wall engagement condition or the temperature difference between room temperature and body temperature may affect a conformational change in its helical diameter or radius.

An alternative means to provide a retracting feature may be explained with reference to the annular frame 30 of the first embodiment 20. The frame 30 may be formed as a hollow torus with an interior channel connected to a longitudinal channel of the catheter 22. By application of fluid pressure at the connector 25 to the channel controlling the inflation of the torus 30, the torus may be expanded to engage the vessel wall and stabilize the cross-sectional area for flow measurements, or alternatively, collapsed to facilitate movement of the distal end 26 within a vessel.

Figure 7A:
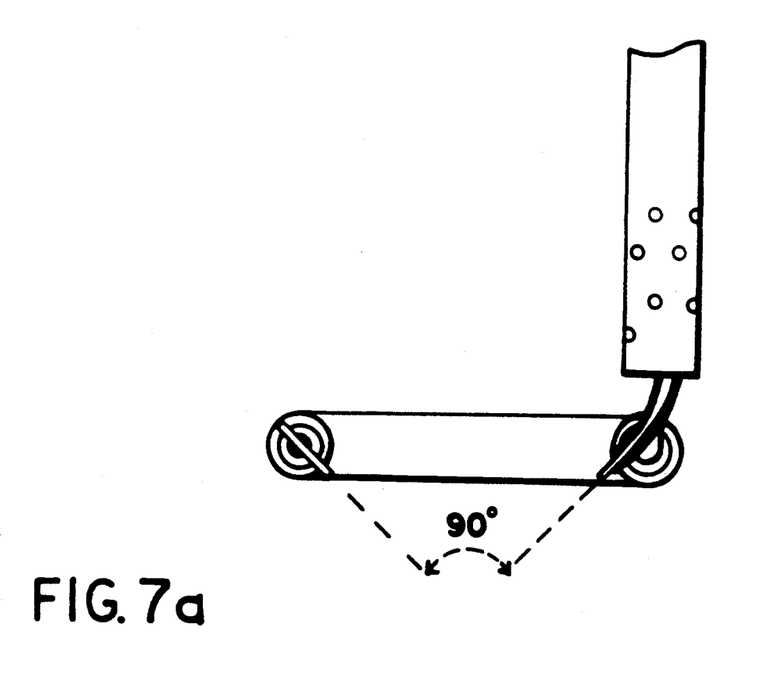
FIG. 7a is an enlarged schematic view of the distal end of another embodiment of the invention.
Figure 7B:
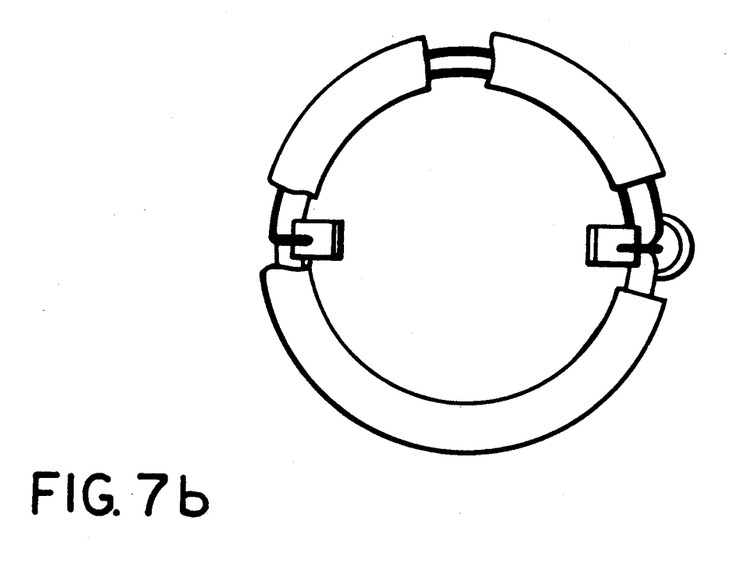

FIG. 7a shows an enlarged schematic view of the distal end 26 of another embodiment of the invention which employs two piezoelectric crystal transducers located on the periphery of the frame 30 in opposing positions. This arrangement allows a continuous wave Doppler measurement of blood flow velocity. FIG. 7b is an axial view of the continuous wave Doppler frame device.

Figure 8:
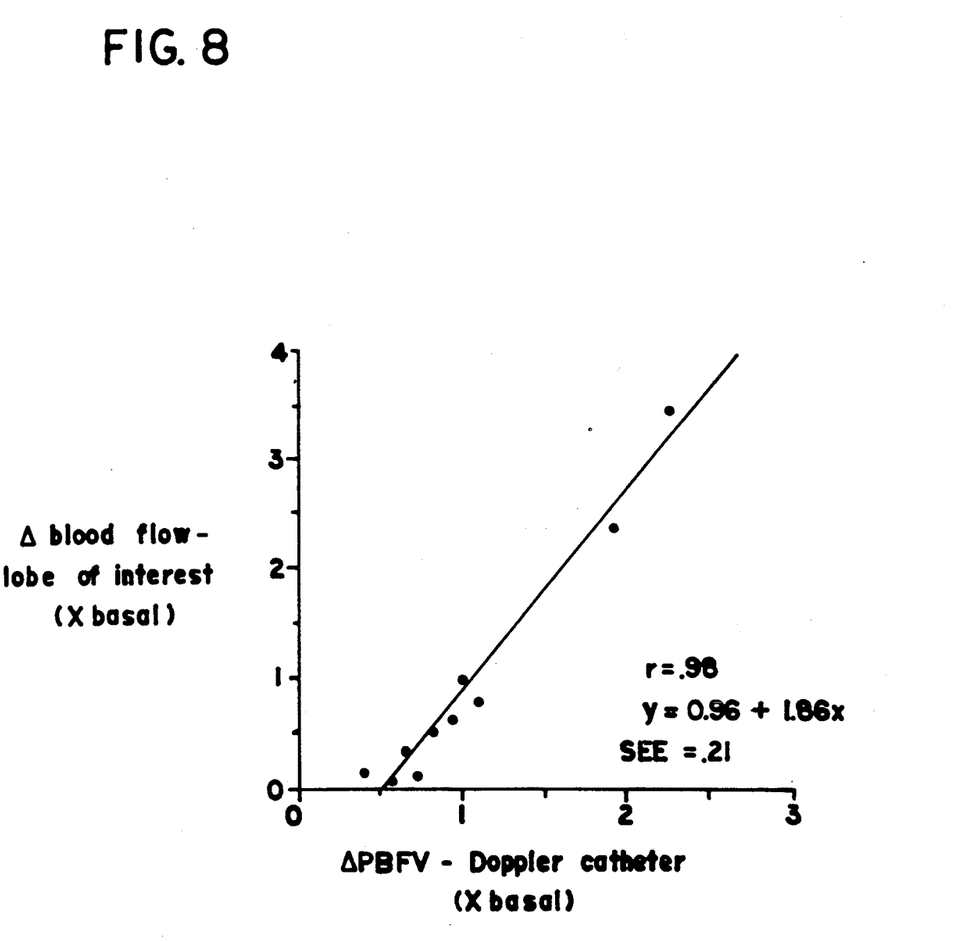
FIG. 8 is a graph of demonstrating the correlation of change of blood flow to a lobe of lung as measured by radioactive microsphere accumulation compared to change in blood flow using a device of this invention.

FIG. 8 is a graph demonstrating the correlation of the change of blood flow to a lobe of lung as measured by radioactive microsphere accumulation compared to change in blood flow velocity (by calculating the velocity from the total flow) using a device 20 of this invention.

Figure 9:
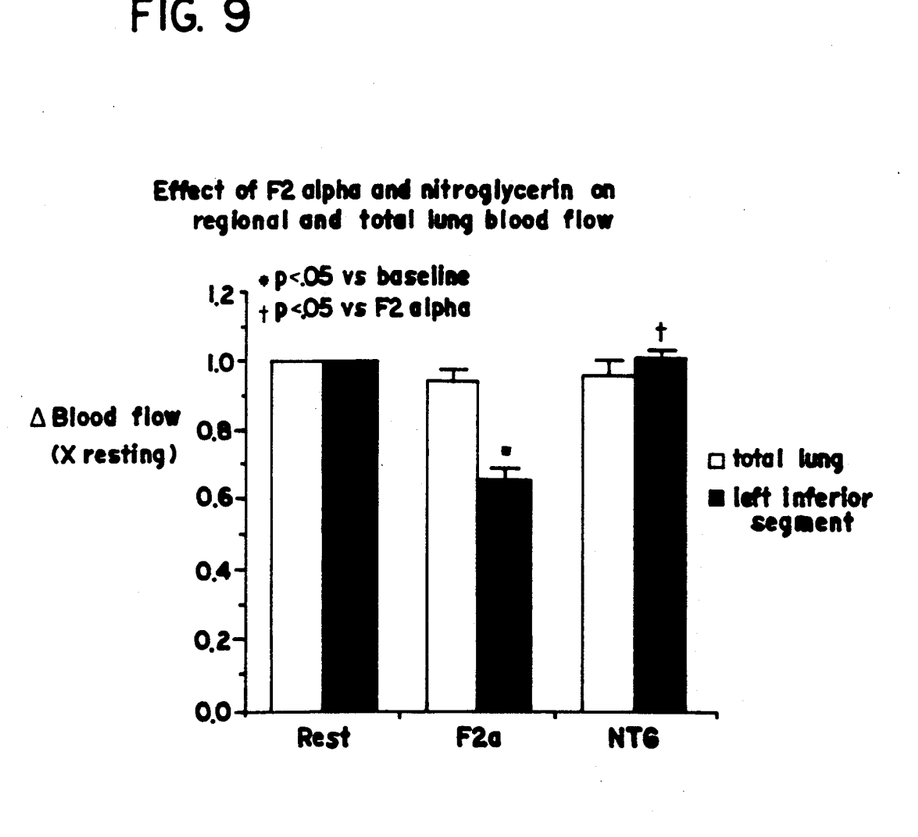
FIG. 9 is a bar graph demonstrating regional lung vascular resistance in response to pharmacological agents as measured by the method of the present invention (solid bar) versus resistance measure by techniques of the prior art (open bar).

FIG. 9 is a bar graph demonstrating regional lung vascular resistance in response to pharmacological agents as measured by the method of the present invention (solid bar) versus resistance measure by techniques of the prior art (open bar).

The device 20 of this invention may alternatively employed to measure blood flow to or from other organs or extremities, such as for example hepatic blood flow, renal blood flow, leg blood flow, or brain blood flow.

EXAMPLE

Table 1 shows the heterogeneous response to a vasocontrictor drug, prostaglandin F 2 alpha. Blood flow velocity to a lung segment was measured using the catheter. Blood flow to the whole lung was measured using the thermodilution technique. Blood flow to the lung segment containing the catheter was reduced significantly more than blood flow to the whole lung after systemic F 2 alpha infusion. Selective infusion of nitroglycerin through the distal end of the catheter reduced pulmonary resistance (increased pulmonary blood flow) only in the segment containing the catheter.

Although the present invention has been described with reference to the preferred embodiments, workers skilled in the art will recognize that changes may be made in form and detail without departing from the spirit and scope of the invention.

TABLE 1

| | Mean pressure | | Segmental velocity | Whole lung blood flow | Segmental resistance | Whole lung resistance |
| --- | --- | --- | --- | --- | --- | --- |
| | Aorta (mmHg) | PA | catheter (X basal) | thermodilution (Xbasal) | (X basal) | (X basal) |
| Basal conditions | 126 | 18 | 1.0 | 1.0 | 1.0 | 1.0 |
| $F_{2alpha}$ | 129 | 27 | 0.66* | 0.96 | 2.2* | 1.7 |
| Nitroglycerine | 125 | 24 | 1.02 | 0.97 | 1.4* | 1.6 |

PA = pulminary artery
*p < .05 vs. whole lung
catheter = segmental blood flow velocity measured with Doppler catheter
thermodilution = thermodilution method for measuring whole lung blood flow
$F_{2alpha}$ a vasoconstrictor, was administered systemically
Nitroglycerine, a vasodilator, was given through the catheter into the lung segment

What is claimed is:

1. A device, suitable for measuring fluid flow within a vessel characterized by generally tubular segments or elastic wall, each of the wall segments having an internal circumference which is normally fluctuating and defining a variable cross-section for the segment, the device comprising:
   a catheter having a distal end suitable for insertion into the means, carried by the catheter adjacent the distal end, for internally stabilizing by engaging the entire internal circumference of one of the segments in order to maintain a constant cross-sectional area of the segment; and
   means, carried by the catheter adjacent the distal end, for detecting fluid velocity within the engaged segment.

2. The device of claim 1, and wherein the means for stabilizing a segment of vessel wall comprises a reinforcement frame of rigidity and perimeter sufficient to engage the segment and secure a constant geometry and dimension without substantially obstructing fluid flow through the segment.

3. The device of claim 2 and wherein the reinforcement frame has a generally annular shape and is oriented with the axis of the annular frame substantially parallel to the longitudinal axis of the catheter.

4. The device of claim 3, and wherein the catheter is connected to the periphery of the annular structure and the means for measuring velocity includes at least one piezoelectric crystal transducer mounted on the catheter adjacent the annular structure.

5. The device of claim 1, and wherein the means for stabilizing includes a means for retracting the means for stabilizing.

6. The device of claim 5, and wherein the means for stabilizing comprises:
   a temperature transformable super-elastic material in a fine crystal structure; and
   wherein temperature transformation of the super elastic material retracts the means for stabilizing.

7. The device of claim 5, and wherein the means for stabilizing a portion of vessel wall includes:
   an inflatable torus connected to the catheter;
   a channel extending longitudinally within the catheter and continuing into the torus structure to provide fluid communication with the torus.

8. The device of claim 5, and wherein the means for stabilizing further comprises:
   a channel longitudinally extending within the catheter; and wherein the means for retracting comprises:
      a guide wire longitudinally slidable within the channel; and
      wherein pressure of the guide wire within the portion of the channel retracts the stabilizing means.

9. The device of claim 1, and wherein the means for measuring velocity include a single piezoelectric crystal transducer capable of ultrasonic velocity measurement by a pulsed Doppler flow measuring system.

10. The device of claim 1, and wherein the means for measuring flow include a pair of piezoelectric crystal transducers capable of ultrasonic velocity measurement by a continuous wave Doppler flow measuring system.

11. The device of claim 1, and wherein the means for detecting include an ultrasonic measurement by a multi-gating Doppler flow measuring system.

12. The device of claim 1, and further comprising: means for measuring pressure adjacent the distal end.

13. The device of claim 12, and wherein the means for measuring pressure comprises a hydraulic fluid pressure measurement system.

14. The device of claim 12, and wherein the means for measuring pressure include a micromanometer.

15. The device of claim 12, and wherein the means for measuring pressure comprises a solid state detector.

16. The device of claim 1 and further comprising: means for delivering a pharmaceutical or biological agent adjacent the distal end.

17. The device of claim 16 and wherein the means for delivering the pharmaceutical agent includes a longitudinal channel of the catheter extending between an outlet adjacent the distal end of the catheter and a fitting adjacent the proximal end of the catheter.

18. The device of claim 1, and wherein the means for stabilizing a portion of vessel wall includes a helical structure of resilient material and the helical structure is oriented such that the helical axis is substantially parallel to the longitudinal axis of the catheter.

19. A method for measuring blood flow in an arterial vessel serving a selected section of vasculature, the method comprising the steps of:
   inserting the distal end of a catheter into the vessel, the catheter having means carried by the catheter adjacent the distal end for engaging the entire internal circumference of a tubular segment of the vessel in order to maintain a constant cross-section of the vessel segment, and having means, carried by the catheter adjacent the distal end, for detecting fluid velocity;
   stabilizing the cross-sectional area of a segment of the wall in the arterial vessel serving the section of pulmonary vasculature by engaging the entire internal circumference with the means for engaging; and
   measuring the velocity of blood flow passing within the stabilized portion of wall.

20. The method of claim 19 wherein the vasculature is pulmonary vasculature and further comprising:
   advancing the stabilizer to the segment of wall to be stabilized.

21. The method of claim 20 and further comprising:
   withdrawing the stabilizing device subsequent to measuring flow.

22. The method of claim 20, wherein the measuring velocity of blood flow includes providing a piezoelectric transducer for ultrasonic Doppler measurement of velocity.

23. The method of claim 20 and further comprising the step of:
   computing the flow of blood based upon the flow velocity and the cross-sectional area within the stabilized wall segment.

* * * * *